US00PP12817P2

(12) United States Plant Patent
Gilford et al.

(10) Patent No.: US PP12,817 P2
(45) Date of Patent: Jul. 30, 2002

(54) STRAWBERRY PLANT NAMED 'MARATHON'

(75) Inventors: Kristie L. Gilford, Dover, FL (US); Bruce D. Mowrey, Watsonville, CA (US); Jorge Campos Garcia, Plant City, FL (US); Thomas M. Sjulin, Aromas; Larry T. Kodama, Freedom, both of CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 09/396,213

(22) Filed: Sep. 15, 1999

(30) Foreign Application Priority Data

Mar. 30, 1999 (CA) ..... 99-1603

(51) Int. Cl.[7] ..... A01H 5/00
(52) U.S. Cl. ..... Plt./209
(58) Field of Search ..... Plt./208, 209

*Primary Examiner*—Bruce R. Campell
*Assistant Examiner*—Michelle Kizilkaya
(74) *Attorney, Agent, or Firm*—Pennie & Edmonds LLP

(57) ABSTRACT

This invention relates to a new and distinct variety of strawberry named 'Marathon', botanically identified as *Fragaria×ananassa*. The closest known varieties are 'Key Largo' (U.S. Plant Pat. No. 8,649), 'Captiva' (U.S. Plant Pat. No. 11,277, allowed) and 'Mirador' (U.S. Plant Pat. No. 11,279, allowed). The new variety is a partially everbearing fruit bearing variety. The variety is distinguished from 'Key Largo', 'Captiva' and 'Mirador' by its strong plant vigor, concave to flat cross section of the leaf, medium leaf blistering, same size diameter of inner to outer calyx, broader than longer fruit ratio length/width, large fruit size and cordate fruit shape.

2 Drawing Sheets

1. BACKGROUND OF THE INVENTION

The new variety originated as a result of a controlled cross between the strawberry plants 'Key Largo' (U.S. Plant Pat. No. 8,649) and 'L3' (unpatented proprietary) in an ongoing breeding program, and was discovered as a seedling in a controlled breeding plot. The original seedling of the new cultivar was asexually propagated by stolons in Shasta County, Calif. Propagules were transplanted to a controlled breeding plot in Valrico, Hillsborough County, Fla. where the new cultivar first fruited in December 1994 and was selected for further evaluation. 'Marathon' was subsequently asexually propagated and underwent further testing in the area of Valrico, Fla. from 1995–1999. This propagation and testing has demonstrated that the combination of traits disclosed herein which characterize the new variety are fixed and retained true to type through successive generations as asexual reproduction.

2. SUMMARY OF THE INVENTION

The present invention relates to a new and distinct variety of strawberry named 'Marathon'. The variety is botanically identified as *Fragaria×ananassa*. The new variety is distinguished from other varieties by a number of characteristics as set forth in Tables 1, 2 and 3.

3. COMPARISON TO CLOSEST VARIETIES

The varieties which we believe to be closest to 'Marathon' from those known to us are 'Key Largo' (U.S. Plant Pat. No. 8,649), 'Captiva' (U.S. Plant Pat. No. 11,277, allowed) and 'Mirador' (U.S. Plant Pat. No. 11,279, allowed). There are several characteristics of 'Marathon' that are different from, or not possessed by 'Key Largo', 'Captiva' or 'Mirador'. Table 1 provides information on the plant and fruit characteristics of the new variety 'Marathon' compared with characteristics of 'Key Largo', 'Captiva' and 'Mirador'. Table 2 provides additional information of the plant and fruit characteristics of the new variety 'Marathon' compared with characteristics of the varieties 'Captiva', 'Key Largo' and 'Mirador'. Table 3 provides isozyme characteristics of the new variety as compared to the varieties 'Key Largo', 'Captiva' and 'Mirador'.

4. BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

5. DESCRIPTION OF THE NEW VARIETY

Figure 1:
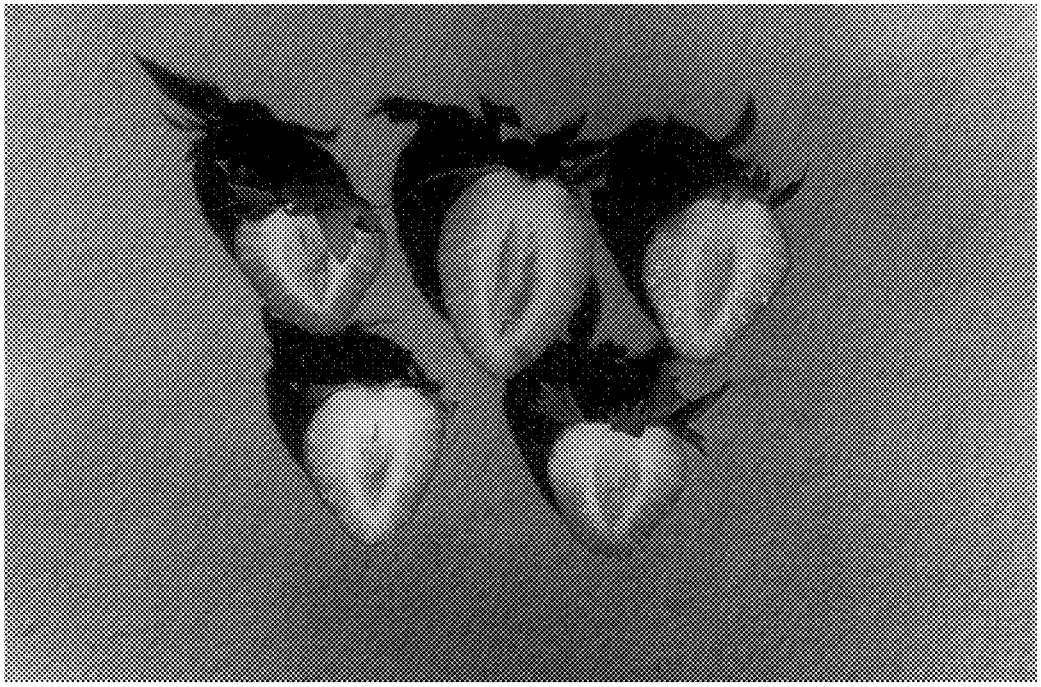
FIG. 1 shows the fruit in longitudinal section, illustrating the typical flesh coloration.
Figure 2:
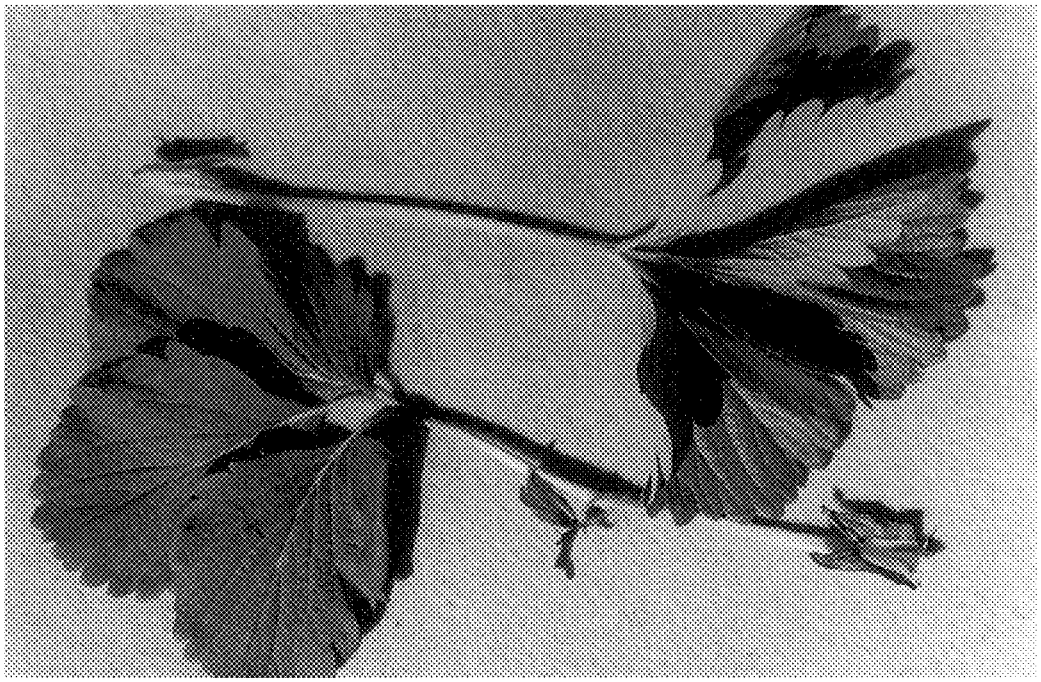
FIG. 2 shows the upper surface of two typical folioles of the new variety.
Figure 3:
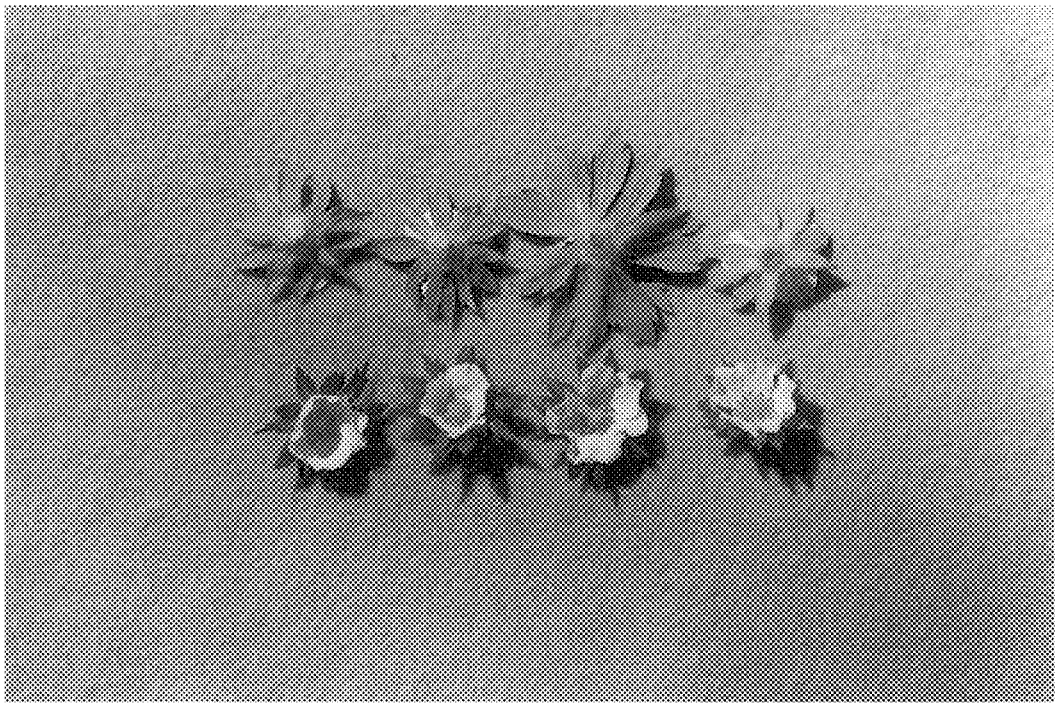
FIG. 3 shows the flower and reproductive organs of the new variety, as well as the size and position of the petals and sepals and the underside of the calyx.
Figure 4:
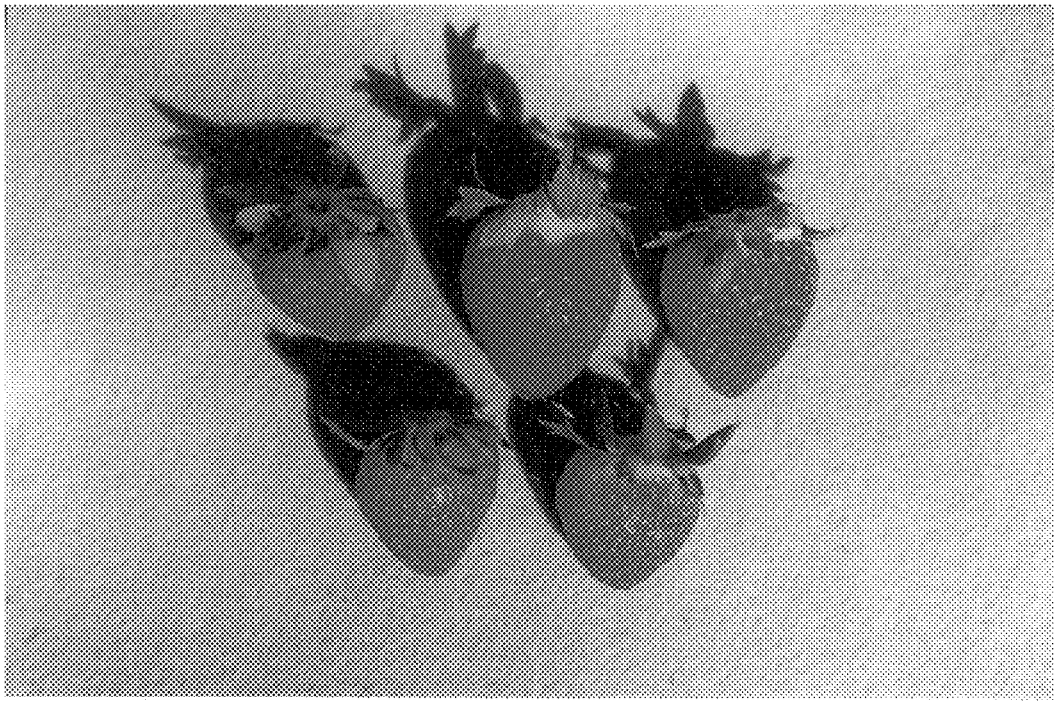
FIG. 4 shows typical whole fruit.

The following detailed description of the new variety is based upon observations taken of plants and fruit grown in Valrico, Fla., U.S.A. Observations of 'Marathon', 'Key Largo', 'Captiva' and 'Mirador' were taken in side by side comparisons in 1999. This description is in accordance with UPOV terminology. Color designations, color descriptions, and other phenotypical descriptions may deviate from the stated values and descriptions depending upon variation in environmental, seasonal, climatic and cultural conditions. Colors are described and the closest matching color ratings are provided using The Royal Horticultural Society (R.H.S.) Colour Chart.

5.1 Propagation

The new variety is principally propagated by way of stolons. Although propagation by stolons is presently preferred, other known methods of propagating strawberry plants may be employed.

5.2 Characteristics of the New Variety

Information the new variety is presented in Tables 1, 2 and 3. In the tables, the flowers described are secondary flowers except where indicated. Petal color of 'Marathon' is white which is not referenced in The Royal Horticultural Society Colour Chart. The fruit described is the secondary fruit on one year old plants. Fruit and flower measurements are an average of both primary and secondary fruit and flowers.

Plants and Foliage

Plants of 'Marathon' are of strong vigor while those of 'Key Largo', 'Captiva' and 'Mirador' are of medium vigor. The average height of 'Marathon' is 21.0 cm, the average diameter is 37.9 cm, and the average number of crowns/plant is 3.8. The upper leaf surface of 'Marathon' is dark green with an R.H.S. color rating of 137B, whereas the color of three comparison varieties have an R.H.S. color rating of 137A. The underside of the leaves of 'Marathon' has a R.H.S. color rating of 138B, while 'Key Largo', 'Captiva' or 'Mirador' have an R.H.S. color rating of 139C. The shape of leaves of 'Marathon' in cross section is concave while those of 'Key Largo' and 'Captiva' and 'Mirador' are slightly concave. The leaves of 'Marathon' exhibit medium interveinal leaf-blistering. 'Marathon' has three leaflets and the leaves are of medium glossiness. The shape of the base of the terminal leaflet is slightly oblique and the teeth of the terminal leaflet are obtuse. The average number of teeth per terminal leaflet is 25.9. The average length and width of the terminal leaflet are 10.6 cm and 11.3 cm, respectively.

The petiole of 'Marathon' has medium pubescence. The pose of the petiole hairs is outwards compared to that of 'Captiva' and 'Key Largo' which is upwards. The average petiole length is 10.4 cm. The petiole color has an R.H.S. color rating of 141D.

The bract frequency is 30% and is typically single compared to that of 'Captiva' and 'Mirador' for which the bracts occur with a 60% frequency. The stipule length and width are 3.7 cm and 2.3 cm, respectively.

The stipule pubescence is medium. Marathon has a medium number to many stolons that are medium to thick in thickness with medium to strong anthocyanin coloration and sparse pubescence.

Flower and Fruit Characteristics

The position of the 'Marathon' inflorescence is beneath the foliage compared to that of 'Mirador' which is above. The flowers are large in size. The average petal length and width are 1.3 cm and 1.4 cm, respectively. The average flower diameter is 4.1 cm. The average calyx diameter is 3.7 cm.

The diameter of 'Marathon's' calyx is larger than the corolla while that of 'Mirador' is the same size. On secondary flowers, the diameter of the inner calyx is the same as the outer calyx. On secondary flowers with 5 to 6 petals, the petals are overlapping. The petal length-to-width ratio on secondary flowers is as broad as they are long compared to that of 'Mirador' which are broader than long.

The fruiting trusses are long in length with an average length of 18.5 cm from the crown to the base of the terminal flower or fruit. The attitude at first picking is prostrate compared to the semi-erect 'Key Largo' and erect 'Mirador'.

Observations of 'Marathon' fruit were taken of secondary fruit on one year old plants. The fruits are predominantly cordate in shape. The fruit ratio of length to maximum width is as broad as long. The fruit are large in size. The average length and width of the fruit are 4.3 cm and 4.3 cm, respectively. There is a slight difference in fruit shape between the primary and secondary fruits. The band without achenes is narrow. The fruit surface has a weak uneveness.

The fruit skin color is an even orange-red with an R.H.S. color rating of 42A and strong glossiness.

The insertion of the achenes is below the surface of the fruit as compared to that of 'Captiva' and 'Mirador' which are level with the surface.

The calyx is set above the fruit and the pose of the calyx segments is spreading. The calyx diameter is larger than the fruit diameter. The adherence of the calyx to the fruit is medium.

The fruit flesh is medium firm when fully ripe. The color of the fruit flesh is medium red with an R.H.S. color rating of 42C. The fruit flesh color is slightly uneven, and the fruit flesh color distribution is marginal and central. The fruit has a medium sized hollow center.

The fruit has a medium sweetness with medium acidity and fine textures.

The time of flowering when 50% of the plants are at first flower is early. Initial flowering occurs in late-October to early-November.

The harvest maturity when 50% of the plants possess ripe fruit is early. Season of harvest is from late-November through early-April. 'Marathon' is a partially everbearing variety.

The average number of stamens is 28.

Anthocyanin coloration is red to purple.

The average number of pedicels/peduncle is 2.3. Average diameter of peduncle is 4.5 mm. Average length of peduncle is 5.8 cm. Average pedicel diameter is 2.7 mm. Average length of pedicels is 11.8 cm. Average petiole diameter is 3.8 mm.

Insertion of achenes is below surface. Achene color is yellow to red (12A to 46A).

Average sepal number is 10.9 and sepal length is 1.5 cm.

Percent brix is 8.3. Amount of pollen produced is abundant and fertile.

TABLE 1

DETAILED COMPARISON OF 'MARATHON', KEY LARGO, 'CAPTIVA' AND 'MIRADOR'

| | MARATHON | CAPTIVA | KEY LARGO | MIRADOR |
|---|---|---|---|---|
| Plant Characteristics | | | | |
| Avg. Height of Plant | 21.0 cm | 13.0 cm | 18.3 cm | 20.0 cm |
| Avg. Spread of Plant | 37.9 cm | 33.1 cm | 39.2 cm | 35.0 cm |
| Avg. Number of Crowns | 3.8 | 4.4 | 4.0 | 3.0 |

TABLE 1-continued

DETAILED COMPARISON OF 'MARATHON', KEY LARGO, 'CAPTIVA' AND 'MIRADOR'

| | MARATHON | CAPTIVA | KEY LARGO | MIRADOR |
|---|---|---|---|---|
| Leaf Characteristics | | | | |
| Terminal Leaflet Width | 11.3 cm | 7.3 cm | 8.9 cm | 9.0 cm |
| Terminal Leaflet Length | 10.6 cm | 7.2 cm | 8.5 cm | 8.3 cm |
| Terminal Leaflet Length/Width Ratio | 0.94 | 0.99 | 0.96 | 0.92 |
| Number of Teeth/Terminal Leaflet | 25.9 | 25.4 | 23.8 | 20.0 |
| Petiole Length | 10.4 | 8.1 | 10.4 | 12.8 |
| Bract Frequency | 30% Typically Single | 60% Typically Single | 30% Typically in pairs | 60% Typically Single |
| Stipule Length | 3.7 | 3.6 | 3.7 | 3.6 |
| Stipule Width | 2.3 | 1.8 | 1.9 | 2.2 |
| Flower Characteristics | | | | |
| Petal Width | 1.4 cm | 1.4 cm | 1.5 cm | 1.6 cm |
| Petal Length | 1.3 cm | 1.4 cm | 1.5 cm | 1.5 cm |
| Petal Length/Width Ratio | 0.93 | 1.00 | 1.00 | 0.94 |
| Flower Diameter | 4.1 cm | 3.6 cm | 3.9 cm | 4.0 cm |
| Calyx Diameter | 3.7 cm | 4.3 cm | 5.1 cm | 4.0 cm |
| Fruit Characteristics | | | | |
| Fruit Width | 4.3 cm | 3.6 cm | 3.5 cm | 3.5 cm |
| Fruit Length | 4.3 cm | 4.1 cm | 4.2 cm | 3.5 cm |
| Fruit Length/Width Ratio | 1.00 | 1.14 | 1.20 | 1.00 |
| Average Berry Weight (g) | 26.5 | 17.8 | 22.4 | 16.3 |
| Fruit Skin Color | Orange Red 42A | Orange Red 45A | Dark Red 46B | Red 45B |
| Fruit Flesh Color | Light Red 42C | Light Red 49C | Light Red 44C | Pale Rose 43B |
| Total Yield (g/plant) | 638 | 369 | 277 | 551 |

TABLE 2

CHARACTERISTICS OF 'MARATHON', 'KEY LARGO', 'CAPTIVA', AND 'MIRADOR'

| | MARATHON | CAPTIVA | KEY LARGO | MIRADOR |
|---|---|---|---|---|
| Plant | | | | |
| Habit | Flat globuse | Flat Globuse | Globuse | Globuse |
| Density | Medium | Medium | Medium | Open |
| Vigor | Strong | Medium | Medium | Medium |
| Leaf | | | | |
| Color of upper side | Dark Green 137B | Dark Green 137A | Dark Green 137A | Dark Green 137A |

TABLE 2-continued

CHARACTERISTICS OF 'MARATHON', 'KEY LARGO', 'CAPTIVA', AND 'MIRADOR'

| | MARATHON | CAPTIVA | KEY LARGO | MIRADOR |
|---|---|---|---|---|
| Color or under side | Light Green 138B | Light Green 139C | Light Green 139C | Light Green 139C |
| Shape in cross section | Concave | Slightly Concave | Slightly Concave | Slightly Concave |
| Interveinal blistering | Medium | Weak | Weak | Weak |
| Glossiness | Medium | Medium | Medium | Medium |
| Number of leaflets | 3 | 3 | 3 | 3 |
| Terminal leaflet margin profile | Revolute | Revolute | Revolute | Revolute |
| Terminal leaflet shape of base | Slightly oblique | Obtuse | Slightly oblique | Slightly oblique |
| Terminal leaflet shape of teeth | Obtuse | Obtuse | Rounded | Rounded |
| Terminal leaflet average number of teeth | 25.9 | 25.4 | 23.8 | 20.0 |
| Petiole pubescence | Medium | Medium | Medium | Medium |
| Petiole pose of hairs | Outwards | Upwards | Upwards | Outwards |
| Petiole Color | 141D | 141C | 141C | 141C |
| Stipule Pubesence | Medium | Medium | Medium | Medium |
| Bracts frequency on petioles | 30% Typically Single | 60% Typically Single | 30% Typically in pairs | 60% Typically Single |
| Stolon | | | | |
| Number | Medium to many | Medium to many | — | Many |
| Anthocyanin coloration | Medium to strong | Strong | — | Medium to strong |
| Thickness | Medium to thick | Medium to thick | — | Thin to medium |
| Pubescence | Sparse | Sparse to medium | — | Sparse to medium |
| Inflorescence | | | | |
| Position relative to foliage | Beneath | Beneath | Beneath | Above |
| Flower size | Large | Medium | Large | Small |
| Diameter of calyx relative to corolla | Larger | Larger | Much larger | Same size |
| Diameter of inner calyx relative to outer | Same size | Smaller | Smaller | Smaller |
| Spacing of petals | Overlapping | Over-lapping | Over-lapping | Over-lapping |
| Fruiting Truss | | | | |
| Attitude at first picking | Prostrate | Prostate | Semi-erect | Erect |
| Length | 18.5 cm | 9.4 cm | 16.6 cm | 17.3 cm |
| Fruit | | | | |
| Predominant shape | Cordate | Conical | Conical | Conical |
| Difference in shapes between primary and secondary fruits | Slight | Slight | Slight | Slight |

TABLE 2-continued

CHARACTERISTICS OF 'MARATHON', 'KEY LARGO', 'CAPTIVA', AND 'MIRADOR'

| | MARATHON | CAPTIVA | KEY LARGO | MIRADOR |
|---|---|---|---|---|
| Band without achenes | Narrow | Narrow | Narrow | Narrow |
| Unevenness of surface | Weak | Weak | Weak | Weak |
| Skin color | Orange Red 42A | Orange red 45A | Dark red 46B | Red 45B |
| Evenness of color | Even | Slightly uneven | Even | slightly uneven |
| Glossiness | Strong | Medium | Strong | Medium |
| Insertion of achenes | Below surface | Level with surface | Below surface | Level with surface |
| Insertion of calyx | Above fruit | Above fruit | Above fruit | Above fruit |
| Pose of the calyx segments | Spreading | Spreading | Reflexed | Spreading |
| Size of calyx in relation to fruit | Larger | Larger | Larger | Larger |
| Firmness of flesh | Medium | Firm | Firm | Firm |
| Color of flesh | Light Red 42C | Light Red 49C | Light Red 44B | Pale Rose 43B |
| Evenness of flesh color | Slightly uneven | Slightly uneven | Slightly uneven | Slightly uneven |
| Distribution of flesh color | Marginal and central | Marginal and central | Marginal and central | Only marginal |
| Hollow center size | Medium | Small | Medium | Medium |
| Sweetness | Medium | Medium | Medium | Medium |
| Texture when tasted | Fine | Fine | Medium | Fine |
| Acidity | Medium | Medium | Medium | Medium |

5.3 Insect and Disease Resistance and Susceptibility

The 'Marathon' variety is moderately susceptible to *Xanthomonas fragariae* and Botrytis fruit rot. The variety is susceptible to Powdery Mildew and Verticillium wilt. The 'Marathon' variety is also susceptible to injury by the two-spotted spider mite (*Tetranychus urticae*), lygus bug (*Lygus hesperus*) and Aphis spp. (Aphids). 'Marathon' is moderately resistant to the Strawberry Mottle Virus.

5.4 ISOZYME ANALYSIS

In addition to the morphological description above, the new cultivar 'Marathon' has been analyzed to obtain an indication of its genetic makeup to provide further means for identifying the new variety and distinguishing it from some other somewhat similar and/or related strawberry varieties. Specifically, leaf samples of 'Marathon', 'Key Largo', 'Captiva' and 'Mirador' were analyzed by electrophoresis for isozyme patterns of the enzymes phosphoglucoisomerase (PGI), leucine aminopeptidase (LAP) and phosphoglucomutase (PGM). See *J. Amer. Soc. Hort. Sci.* 106:684–687. Isozyme characterization of the four varieties is presented in Table 3, with the letters representing the banding patterns for each enzyme as designated in the above-identified article.

TABLE 3

ISOZYME ANALYSIS FOR 'MARATHON', 'CAPTIVA', 'KEY LARGO' AND 'MIRADOR'

| Locus | MARATHON | CAPTIVA | KEY LARGO | MIRADOR |
|---|---|---|---|---|
| PGI | A1 | A2 | A1 | A3 |
| LAP | B3 | B3 | B3 | B3* |
| PGM | C4 | C2 | C4 | C4 |

*With a slower migration band staining more weakly than typical B3 pattern.

What is claimed is:

1. A new and distinct variety of strawberry plant, substantially as shown and described.

* * * * *